United States Patent
Kashiwagi et al.

(10) Patent No.: US 6,575,948 B1
(45) Date of Patent: Jun. 10, 2003

(54) SANITARY NAPKIN

(75) Inventors: Masahiro Kashiwagi, Kagawa-ken (JP); Keiichi Jibiki, Kagawa-ken (JP)

(73) Assignee: Uni-Charm Corp., Ehime-ken (JP)

( * ) Notice: Subject to any disclaimer, the term of this patent is extended or adjusted under 35 U.S.C. 154(b) by 0 days.

(21) Appl. No.: 09/352,057

(22) Filed: Jul. 14, 1999

(30) Foreign Application Priority Data

Jul. 15, 1998 (JP) .......................................... 10-200380

(51) Int. Cl.⁷ ................................................ A61F 13/15
(52) U.S. Cl. ........................ 604/385.101; 604/385.17; 604/378
(58) Field of Search ................... 604/385.17, 385.04, 604/385.01, 378–380, 385.101

(56) References Cited

U.S. PATENT DOCUMENTS

| | | | |
|---|---|---|---|
| 4,723,953 A | | 2/1988 | Rosenbaum et al. |
| 4,758,240 A | | 7/1988 | Glassman |
| 5,197,959 A | * | 3/1993 | Buell .................... 604/385.1 |
| 5,514,120 A | * | 5/1996 | Johnston et al. ............ 604/378 |
| 5,591,150 A | * | 1/1997 | Olsen ..................... 604/385.1 |
| 5,846,230 A | * | 12/1998 | Osborn .................... 604/378 |

FOREIGN PATENT DOCUMENTS

| | | |
|---|---|---|
| GB | 2 296 437 A | 7/1996 |
| GB | 2 296 438 A | 7/1996 |
| GB | 2 319 186 A | 5/1998 |
| JP | A-2-11138 | 1/1990 |

OTHER PUBLICATIONS

Copy of European Search Report mailed Jan. 30, 2001.

* cited by examiner

*Primary Examiner*—Weilun Lo
*Assistant Examiner*—C. Lynne Anderson
(74) *Attorney, Agent, or Firm*—Butzel Long

(57) ABSTRACT

A sanitary napkin has an absorbent core convexly curved upward and the absorbent core is provided on its lower side with a pad adapted to hold a curved shape of the absorbent core. The pad is formed on its upper side with a plurality of projections and continuous troughs so that the projections are bonded to the lower side of the absorbent core and the troughs form a continuous tunnel between the absorbent core and the pad. The pad thus formed improves a breathability of the sanitary napkin during its use.

14 Claims, 5 Drawing Sheets

SANITARY NAPKIN

BACKGROUND OF THE INVENTION

This invention relates to a sanitary napkin for personal feminine care which absorbs menstrual fluids or similar exudates.

Japanese Patent Application Disclosure Gazette (Kokai) No. Hei2-11138 discloses a sanitary napkin provided with bending means referred to as "deformation inducing element" adapted to deform the sanitary napkin so that its side facing a wearer's body may be curved convexly upward when the sanitary napkin is put on the wearer's body. Such a deformation inducing means is a formed material such polyethylene foam, other plastic sheet or cardboard having substantially the same size as that of the sanitary napkin. An absorbent core of the sanitary napkin and a backsheet covering a lower surface of the absorbent core are in close contact with the deformation inducing element and are deformed together with the deformation inducing element to form a convex curve.

With the element functioning to induce a convex deformation of the sanitary napkin normally kept in close contact with the lower surface of the absorbent core directly or indirectly with interposition of the backsheet as in the case of the above-mentioned sanitary napkin, a thickness of the deformation inducing element is added to a thickness of the absorbent core itself. Consequently, the absorbent core can not offer a breathability in the direction of its thickness sufficient to avoid a stuffiness from which the wearer might suffer when she wears the sanitary napkin.

SUMMARY OF THE INVENTION

It is an object of the present invention to provide a sanitary napkin provided on its lower side with a pad serving to hold the absorbent core in its shape curved convexly toward a body-facing side without deteriorating a breathability desired for the sanitary napkin.

According to the present invention, there is provided a sanitary napkin having a longitudinal direction and a transverse direction, the sanitary napkin comprising a liquid-pervious topsheet, a liquid-impervious backsheet and a liquid-absorbent core disposed between the topsheet and the backsheet, a cross-section of the absorbent core cut along the transverse direction being curved convexly toward a body-facing side and a pad curved convexly toward the body-facing side substantially in conformity with the absorbent core being placed against a lower surface of the absorbent core in a curved zone thereof wherein:

the surface of the pad placed against the absorbent core is composed of a plurality of intermittently arranged projections and a continuous trough comprising a plurality of trough sections each defined between each pair of the adjacent projections so that the trough sections extend longitudinally as well as transversely of the absorbent core to intersect one another and opposite ends of each trough section terminate at a peripheral edge of the pad, and the pad is placed against the lower surface of the absorbent core at tops of the projections so that a plurality of tunnel sections each having opposite ends thereof opened at the peripheral edge of the pad are formed between the continuous trough and the lower surface of the absorbent core.

According to one embodiment of the present invention, the pad lies in the transversely middle zone of the sanitary napkin so that imaginary lines extending in parallel to a center line dividing a width of the sanitary napkin in two are alternately interrupted by the projections and through of the pad.

According to another embodiment of the present invention, the pad is made of thermoplastic synthetic fibers.

According to still another embodiment of the present invention, the pad is made of crimped thermoplastic conjugated fibers.

According to yet another embodiment of the present invention, the pad is made of thermoplastic hollow fibers.

According to further another embodiment of the present invention, a height as measured from a bottom of the trough to a top of the projection is 0.3~3 mm.

According to another embodiment of the present invention, the trough rectilinearly extends obliquely across the longitudinal direction of the absorbent core.

According to still another embodiment of the present invention, the trough meanders so as to obliquely intersect the longitudinal direction of the absorbent core.

According to yet another embodiment of the present invention, the pad is relatively thick at the projections and relatively thin at the trough.

According to further another embodiment of the present invention, the pad is made of thermoplastic synthetic fibers, having a relatively low density at the projections and a relatively high density at the trough.

According to an additional embodiment of the present invention, the pad, in its transversely curved state, presents a rigidity gradually decreasing from its transversely middle zone to its transversely opposite side edges.

According to still additional embodiment of the present invention, the pad is made of a foamed plastic sheet.

According to further additional embodiment of the present invention, the pad is made of a compressed foam plastic sheet.

DETAILED DESCRIPTION OF THE PREFERRED EMBODIMENTS

Details of a sanitary napkin according to the present invention will be more fully understood from the description given hereunder with reference to the accompanying drawings.

Figure 1:
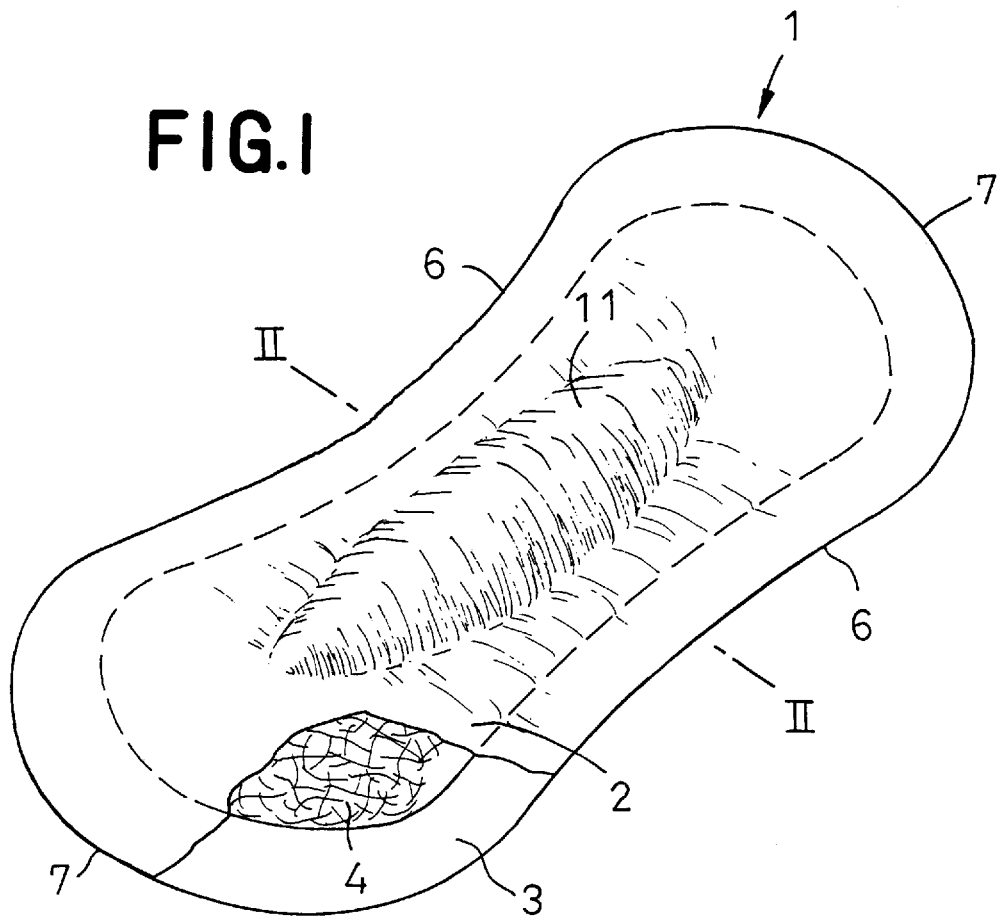
FIG. 1 is a perspective view showing a partially cut away sanitary napkin according to the present invention.
Figure 2:
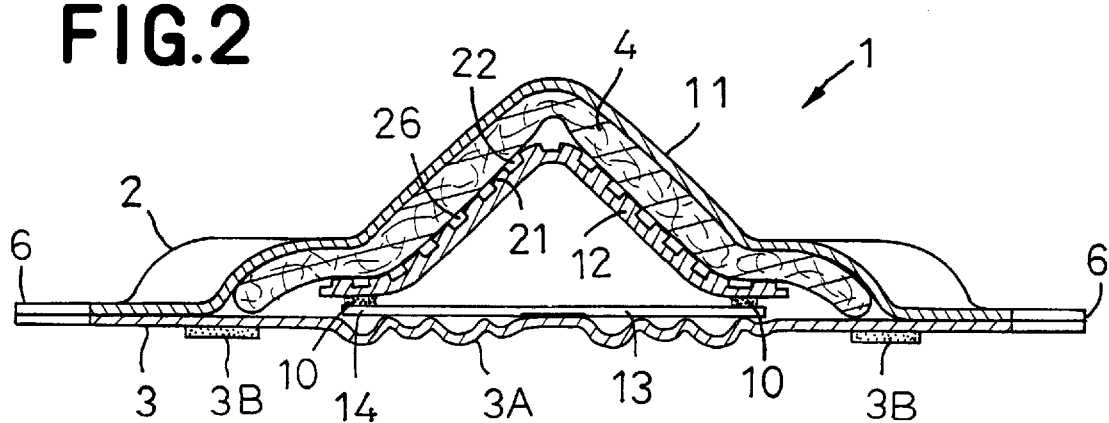
FIG. 2 is a sectional view taken along a line II—II in FIG. 1.

FIG. 1 is a perspective view showing a partially cut away sanitary napkin according to the present invention and FIG. 2 is a sectional view taken along a line II—II in FIG. 1. A sanitary napkin 1 comprises a liquid-pervious topsheet 2, a liquid-impervious backsheet 3 and a liquid-absorbent core 4 disposed between these two sheets 2, 3. The topsheet 2 and the backsheet 3 extend outward beyond a peripheral edge of the absorbent core 4 and are placed upon and bonded to each other along their respective extensions. The sanitary napkin 1 has a contour defined by a pair of side edges 6 extending longitudinally of the sanitary napkin 1 and a pair of ends 7 extending transversely of the sanitary napkin 1 so as to intersect the side edges 6. The sanitary napkin 1 is formed in its longitudinal middle with a protuberant zone 11 convexly curved from the backsheet 3 toward the topsheet 2, that is, toward a body-facing side and extending transversely of the sanitary napkin 1.

As will be seen in FIG. 2, the absorbent core 4 of the sanitary napkin 1 is curved convexly or bent in an inverted V-shape toward the body-facing side. On a lower side, that is, a garment-facing side of the absorbent core 4, there are provided a pad 12 adapted to be curved convexly or bent in the inverted V-shape in the same manner as the absorbent core 4 and elastic members 13 extending transversely of the absorbent core 4. Regarding the pad 12, a flat pad may be previously shaped in a curved shape and the elastic members 13 may be secured to transversely opposite side edges of the pad thus causing pad 12 to hold its shape. Alternatively, the elastic members 13 may be secured in a longitudinally extended state to the side edges of the pad 12 so that the pad 12 may present the curved shape as the elastic members 13 contract. The topsheet 2 is bonded to the absorbent core 4 which is, in turn, bonded to the pad 12 so that both the topsheet 2 and the absorbent core 4 may be contoured in conformity with the pad 12. The absorbent core 4 and/or the pad 12 may be provided in their transversely middle zones with a suitable deformation guiding means such as longitudinally extending grooves to facilitate curving or bending thereof. The backsheet 3 is formed in its transversely middle zone with pleats extending longitudinally of the sanitary napkin 1 so that the curved absorbent core 4 tending to restore its flat state should not be prevented from deforming to spread transversely thereof. The lower side of the backsheet 3 is applied in the vicinities of the respective side edges 6 with adhesive agent 3B so that the sanitary napkin 1 can be fasten to shorts worn by the user.

Figure 3:
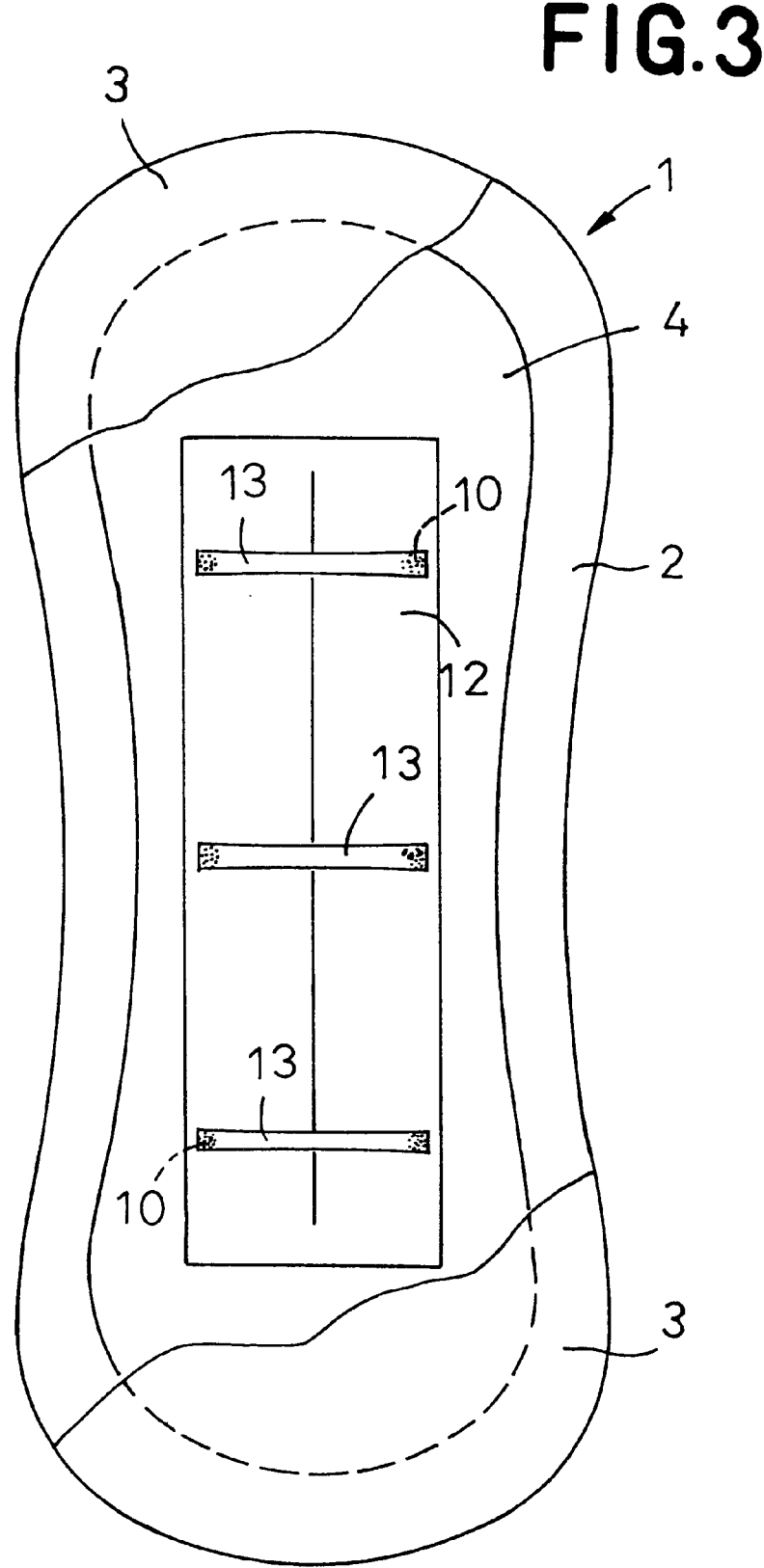
FIG. 3 is a plan view showing a lower side of the partially cut away napkin.

FIG. 3 is a plan view showing the lower side of the partially cut away sanitary napkin 1. The elastic members 13 are secured to the lower side of the pad 12 by means of hot melt adhesive 10. It should be understood that the number of the elastic members 13 may be selected depending on a longitudinal dimension of the pad 12. It is also possible without departing from the spirit and scope of the present invention to eliminate use of the elastic members 13. This is the case in which the pad 12 is previously molded in convex or inverted V-shape and then such pad 12 is bonded to the absorbent core to form the protuberant zone 11.

Figure 4:
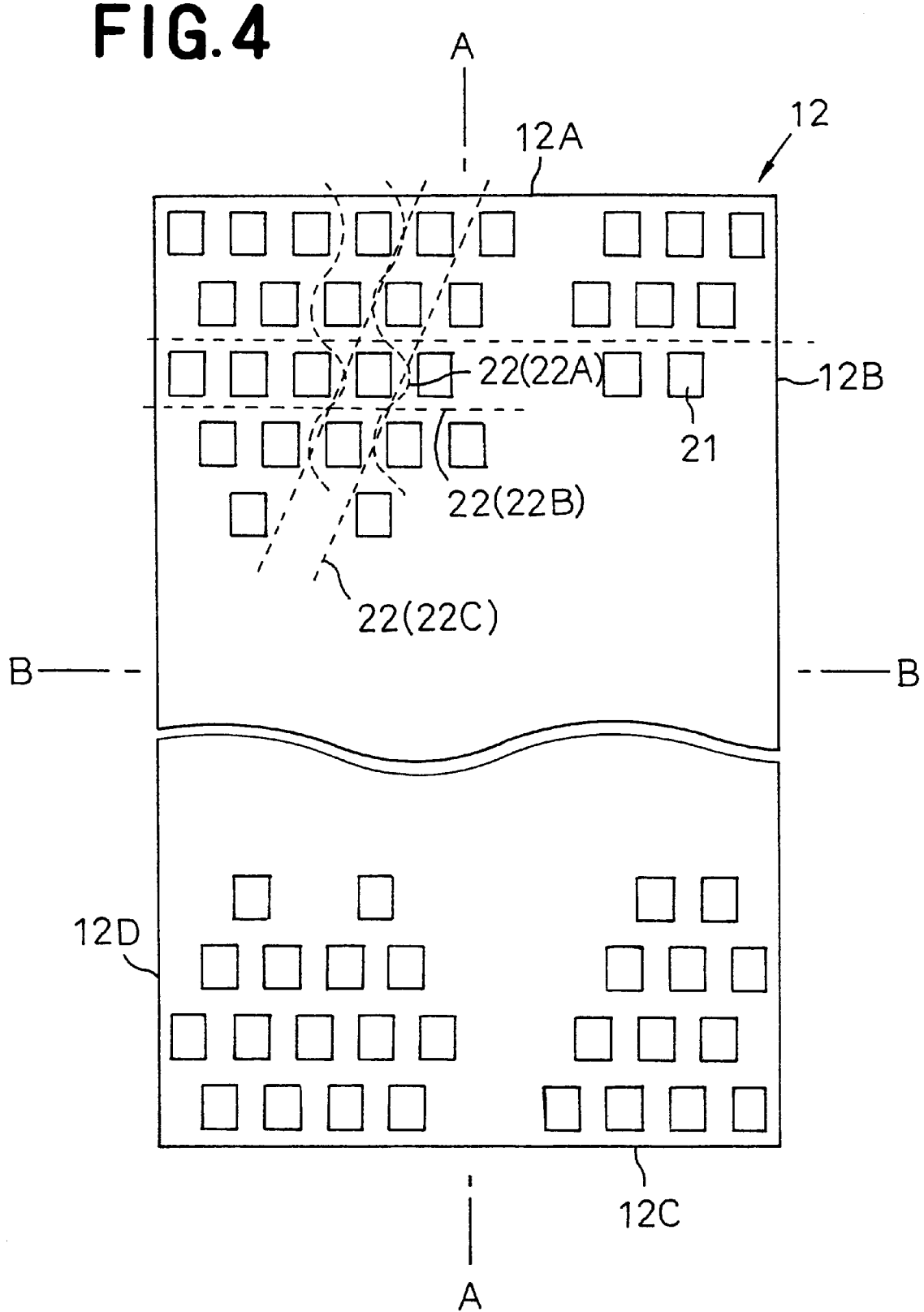
FIG. 4 is a plan view of a pad.
Figure 5:
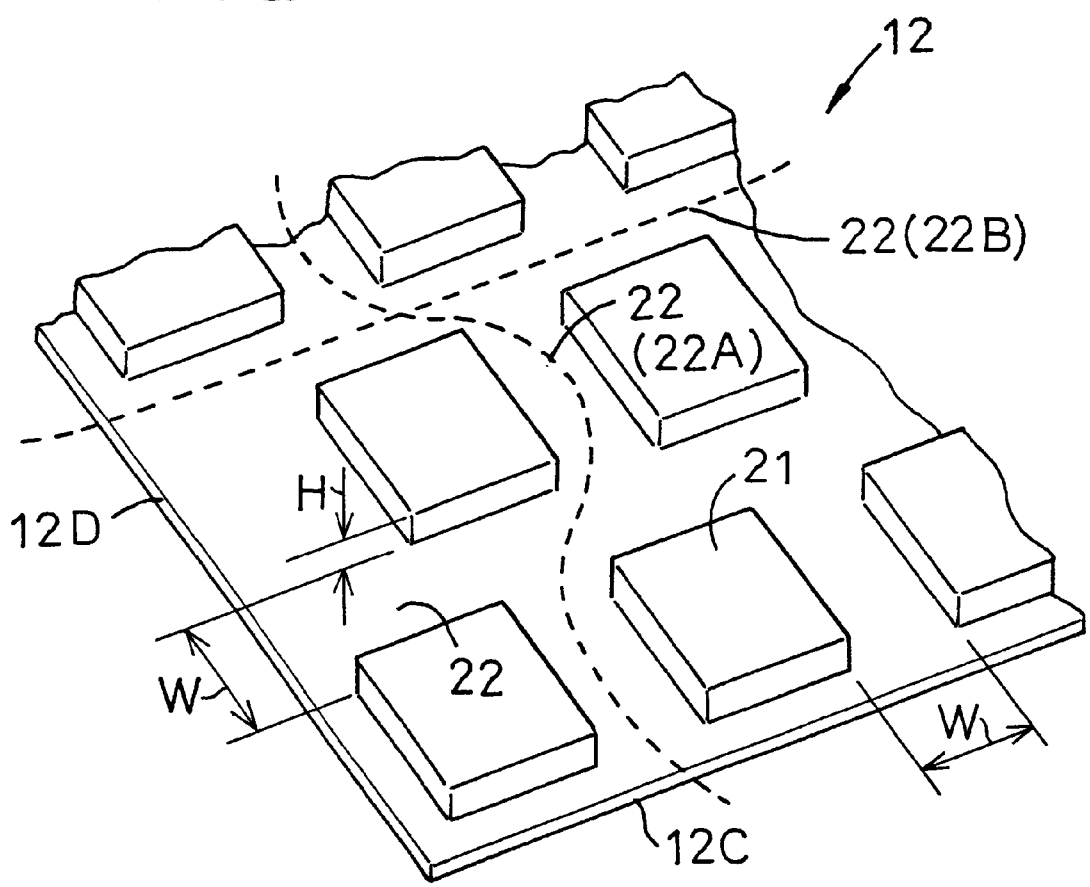
FIG. 5 is a fragmentary perspective view of the pad.

FIG. 4 is a plan view and FIG. 5 is a fragmentary perspective view both showing the pad 12 in its flat state. While the pad 12 is not limited to any particular shape, it is generally preferred to provide the pad 12 of rectangular or square shape. According to the specific embodiment shown, the pad 12 is of a rectangular shape having a first center line A—A dividing its width in two and a second center line B—B dividing its length. Such pad 12 may be formed by a carded web or nonwoven fabric output from a card, a foamed plastic sheet or plastic film. On the upper surface of the pad 12 facing the lower surface of the absorbent core 4, a plurality of projections 21 in the form of square pillars and a continuous troughs' 22 are uniformly distributed. The projections 21 are arranged in parallel to both the first center line A—A and the second center line B—B and the troughs' 22 are defined between each pair of the adjacent projections 21 so as to extend longitudinally as well as transversely of the sanitary napkin 1. The continuous troughs' 22 arrives at four sides 12A~12D defining a peripheral edge of the pad 12. Of the continuous troughs' 22, sections 22A extending longitudinally of the pad 12 meander substantially in the direction of the first center line A—A as indicated by chain lines. Sections 22B extending transversely of the pad 12 extend in parallel to the second center line B—B and intersect the sections 22A. Sections 22C obliquely extending intersect both the first center-line A—A and the second center-line B—B. A height as measured from a bottom of these sections 22A, 22B, 22C to a top of each projections 21 is 0.3~3 mm, preferably 0.5~1.5 mm. A width of the sections 22A, 22B is 0.3~5 mm, preferably 1~3 mm so far as these sections are in a relatively flat state. The pad 12 is bonded in the vicinities of the tops of the respective projections 21 to the lower surface of the absorbent core 4 by means of hot melt adhesive (not shown). On the other hand, the troughs' 22 are spaced from the absorbent core 4 to provide a continuous tunnel 26 comprising a plurality of tunnel sections (See FIG. 2) defined between the troughs' 22 and the lower surface of the absorbent core 4 and extending between four sides of the pad 12 so that each of the tunnel sections 26 may have its opposite ends opened at any two of the four sides 12A~12D. While each of the projections 21 is shown to present a rectangular shape as viewed in the plan view, it may also present the other plan shape such as square, circular or oval shape. Arrangement of the projections 21 may be regular or irregular. Depending on the arrangement of the projections 21, the sections of the continuous troughs' 22 extend rectilinearly or in zigzag.

In the sanitary napkin 1 of such arrangement, a thickness of the absorbent core 4 increases by a thickness of the pad 12. However, an amount of wet air accumulated within the absorbent core 4 is forced out from the absorbent core 4 and an amount of relatively dry air is taken into the absorbent core 4 through the tunnel 26 formed between the pad 12 and the absorbent core 4 as the sanitary napkin 1 is repeatedly deformed under a body weight. In this manner, the sanitary napkin 1 according to this invention allows a stuffiness from which the wearer otherwise would suffer to be alleviated or even eliminated. Even when the sanitary napkin 1 is deformed more or less, the tunnels 26 are not readily collapsed because the respective tunnels 26 extend between each pair of the adjacent sides or opposite sides of the rectangular pad 12 and the opposite ends of each tunnel section 26 are opened at two of the four sides defining the rectangular pad 12.

When the pad 12 is made of a carded web or nonwoven fabric, thermoplastic synthetic fibers are preferably used so that the pad 12 can maintain a desired rigidity even in its wetted state. One of crimped conjugated fibers and hollow fibers or a mixture of them may be used as the synthetic fibers to improve an elasticity of the pad 12 as well as fitting thereof to the wearer's skin. The troughs' 22 of the pad 12 may be formed, for example, by locally compressing the web or nonwoven fabric having a basis weight of 50~200 g/m$^2$, preferably 80~160 g/m$^2$ under heating. The troughs' 22 obtained in this manner are thinner than the projections 21 and relatively high in its density as well as in its rigidity.

The projections 21 and the troughs' 22 of the pad 12 are preferably arranged so that the projections 21 of low rigidity and the trough sections 22 of high rigidity alternate on an imaginary line extending in parallel to the first center line A—A longitudinally of the absorbent core 4. In other words, they are preferably arranged so that the imaginary line is alternately interrupted by the projections 21 and the trough sections 22. With this unique arrangement, when the pad 12 is curved transversely thereof, the top of the pad 12 advantageously tends to present a radius of curvature larger than in the case of the pad 12 having a uniformly high or low rigidity. Specifically, the top of the pad 12 tends to describe a smoothly convex curve rather than a relatively sharp inverted V-shape. The sanitary napkin 1 using the pad 12 of which the top has a relatively large radius of curvature is not only advantageous in its breathability but also its fitness against wearer's vaginal orifice over a larger area and thereby substantially improve an absorption rate for menstrual discharge.

Figure 6:
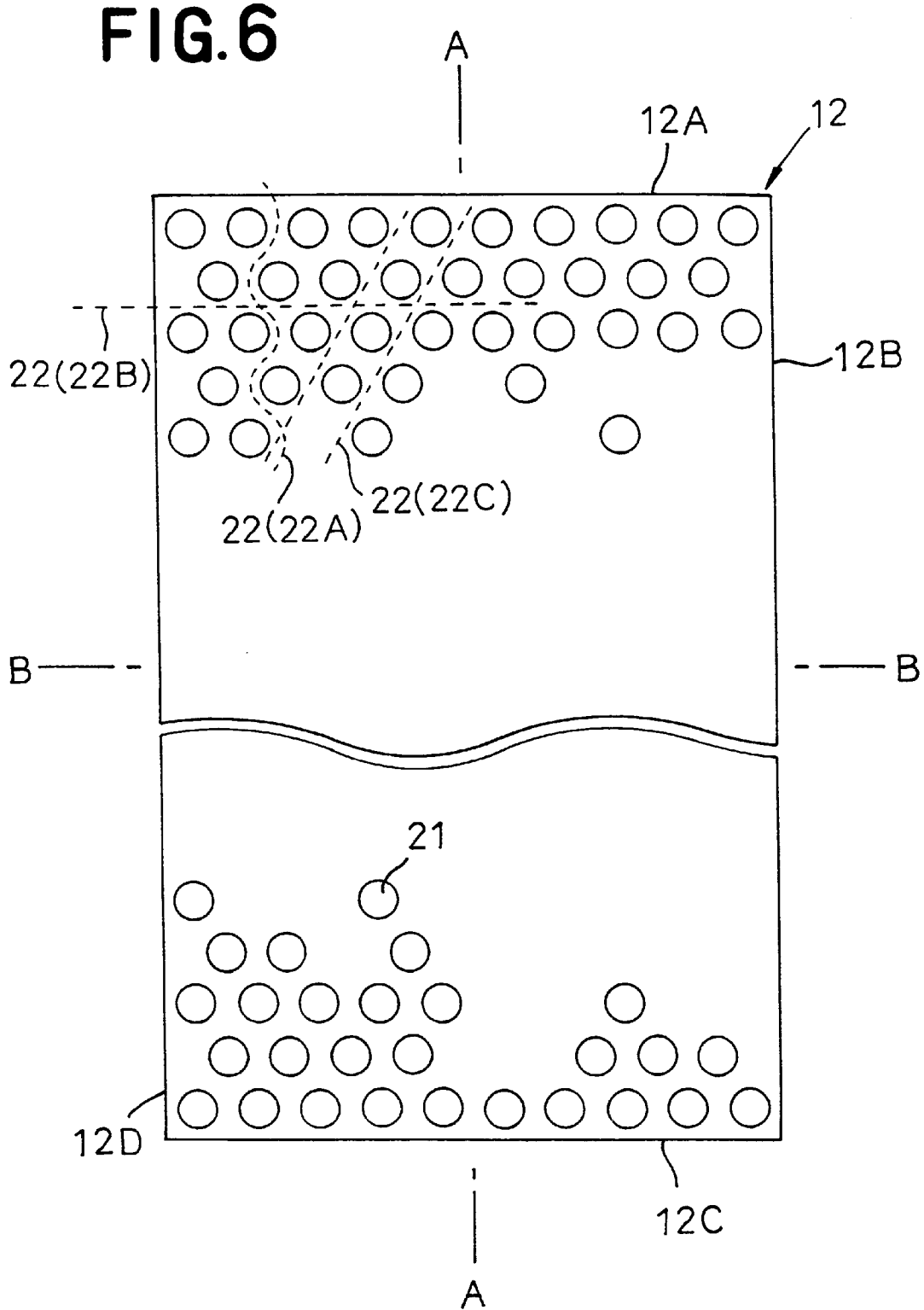
FIG. 6 is a view similar to FIG. 4 showing an alternative embodiment of the pad.

FIG. 6 is a view similar to FIG. 4 showing an alternative embodiment of the pad 12. This specific embodiment of the pad 12 has cylindrical projections 21 replacing the square pillar-like projections 21, trough sections 22A meandering in the direction of the first center line A—A as indicated by chain lines, trough sections 22B rectilinearly extending in parallel to the second center line B—B and rectilinear trough sections 22C obliquely extending to intersect both the first center line A—A and the second center line B—B.

To exploit the present invention, a nonwoven fabric or apertured plastic film may be used as stock material for the topsheet 2 and a plastic film may be used for the backsheet 3. The absorbent core 4 may be formed by covering fluff pulp or a mixture of fluff pulp and superabsorptive polymer particles with tissue paper. To bond the respective members together, adhesive agent such as hot melt adhesive or, for the heat-sealable members, the heat-sealing technique may be adopted.

The sanitary napkin according to the present invention is free from any apprehension that the sanitary napkin might become stuffy during its use in spite of the fact that the presence of the pad increases the thickness of the absorbent core 4 because the shape holding pad bonded to the lower surface of the absorbent core forms the breathable tunnel between the pad and the lower surface of the absorbent core.

what is claimed is:

1. A sanitary napkin having a longitudinal direction and a transverse direction, said sanitary napkin comprising:

a liquid-pervious topsheet;

a liquid-impervious backsheet;

a liquid-absorbent core disposed between the liquid-pervious topsheet and the liquid-impervious backsheet, said liquid-absorbent core having a transverse cross-section which is curved toward said liquid-pervious topsheet; and a pad positioned against a lower surface of said liquid-absorbent core in a curved zone thereof, said pad being convexly curved toward said liquid-pervious topsheet and in substantial conformity with the liquid-absorbent core, a surface of said pad which is placed against said liquid-absorbent core comprises a plurality of discrete projections and continuous troughs that include a plurality of trough sections each defined between adjacent ones of said plurality of projections so that the trough sections extend longitudinally as well as transversely of said liquid-absorbent core to intersect one another, and opposite ends of each trough section terminating at a peripheral edge of said pad, said pad being placed against said lower surface of said liquid-absorbent core at tops of said plurality of projections so that a plurality of tunnel sections each having opposite ends opened at said peripheral edge of said pad are formed between said continuous troughs and said lower surface of said liquid-absorbent core.

2. A sanitary napkin according to claim 1, wherein said pad lies in a transversely middle zone of said sanitary napkin so that imaginary reference lines which extend parallel to a center line dividing a width of said sanitary napkin in two are alternately interrupted by said plurality of projections and troughs of said pad.

3. A sanitary napkin according to claim 1, wherein said pad is made of thermoplastic synthetic fibers.

4. A sanitary napkin according to claim 1, wherein said pad is made of crimped thermoplastic conjugated fibers.

5. A sanitary napkin according to claim 1, wherein said pad is made of thermoplastic hollow fibers.

6. A sanitary napkin according to claim 1, wherein a height of each of said plurality of projections as measured from a bottom of said troughs to a top of each of said plurality of projections is about 0.3 to about 3 mm.

7. A sanitary napkin according to claim 1, wherein said troughs rectilinearly extend obliquely across said longitudinal direction of said liquid-absorbent core.

8. A sanitary napkin according to claim 1, wherein said troughs meander so as to obliquely intersect said longitudinal direction of said liquid-absorbent core.

9. A sanitary napkin according to claim 1, wherein said pad is thicker at said projections than at said troughs.

10. A sanitary napkin according to claim 1, wherein said pad is made of thermoplastic synthetic fibers, having a lower density at said projections than at said troughs.

11. A sanitary napkin according to claim 1, wherein said pad, in its transversely curved state, has a rigidity which gradually decreases from its transversely middle zone to its transversely opposite side edges.

12. A sanitary napkin according to claim 1, wherein said pad is made of a foamed plastic sheet.

13. A sanitary napkin according to claim 1, wherein said pad is made of a compressed foam plastic sheet.

14. A sanitary napkin according to claim 1, wherein the plurality of discrete projections are arranged in a two-dimensional array.

* * * * *